United States Patent
Wang

(10) Patent No.: US 7,060,498 B1
(45) Date of Patent: Jun. 13, 2006

(54) POLYCATIONIC WATER SOLUBLE COPOLYMER AND METHOD FOR TRANSFERRING POLYANIONIC MACROMOLECULES ACROSS BIOLOGICAL BARRIERS

(75) Inventor: Laixin Wang, Salt Lake City, UT (US)

(73) Assignee: Genta Salus LLC, Berkeley Heights, NJ (US)

( * ) Notice: Subject to any disclaimer, the term of this patent is extended or adjusted under 35 U.S.C. 154(b) by 212 days.

(21) Appl. No.: 09/996,507

(22) Filed: Nov. 28, 2001

(51) Int. Cl.
*C12N 15/63* (2006.01)
*C07H 21/02* (2006.01)
*A61K 31/70* (2006.01)

(52) U.S. Cl. .................. 435/455; 536/23.1; 514/44
(58) Field of Classification Search ............... 435/455, 435/320.1; 424/490–3, 78.18, 486; 536/23.1, 536/24.5
See application file for complete search history.

(56) References Cited

U.S. PATENT DOCUMENTS

| | | | |
|---|---|---|---|
| 5,079,237 A | 1/1992 | Husu et al. | |
| 5,256,652 A | 10/1993 | El-Rashidy | |
| 5,275,824 A | 1/1994 | Carli et al. | |
| 5,380,536 A | 1/1995 | Hubbell et al. | |
| 5,389,381 A | 2/1995 | Phillips et al. | |
| 5,567,410 A | 10/1996 | Torchilin et al. | |
| 5,656,611 A | 8/1997 | Kabanov et al. | |
| 5,661,025 A | 8/1997 | Szoka, Jr. et al. | |
| 5,681,747 A * | 10/1997 | Boggs et al. ............... | 435/375 |
| 5,714,166 A | 2/1998 | Tomalia et al. | |
| 5,777,078 A * | 7/1998 | Bayley et al. .............. | 530/350 |
| 5,820,882 A | 10/1998 | Hubbell et al. | |
| 6,113,946 A | 9/2000 | Szoka, Jr. et al. | |
| 6,153,597 A | 11/2000 | Blanche et al. | |
| 6,221,959 B1 * | 4/2001 | Kabanov et al. ........... | 525/54.2 |
| 6,231,892 B1 | 5/2001 | Hubbell et al. | |
| 6,300,317 B1 | 10/2001 | Szoka, Jr. et al. | |
| 6,312,727 B1 | 11/2001 | Schacht et al. | |
| 6,333,051 B1 | 12/2001 | Kabanov et al. | |
| 6,440,743 B1 | 8/2002 | Kabanov et al. | |
| 2001/0005717 A1 * | 6/2001 | Wagner et al. ................ | 514/44 |

FOREIGN PATENT DOCUMENTS

WO    WO 98/19710    *    5/1998

OTHER PUBLICATIONS

Antonelli et al (Theoretical and Applied Genetics (1990 80(3): 395-401.*
Taylor et al (DNA and Cell Biol. 21(12): 963-977 (2002).*
GenBank Accession No. AAP45055 ( May 6, 2003).*
Kircheis et al (Gene Therapy 4: 409-418, 1977).*
Akhtar, Saghir, et al. "The Delivery of Antisense Therapeutics," Advanced Drug Delivery Reviews 44, (2000), 3-21.
Akiyama, Yoshitsugu, et al., "Synthesis of Poly(ethylene glycol)-block-poly(ethylenimine) Possesssing an Acetal Group at the PEG End," Macromolecules, 2000, 33, 5841-5845.
Abdallah, Bassima, et al., "A Powerful nonviral Vector for In Vivo Gene Transfer Into the Adult Mammalian Brain: Polyethylenimine," Human Gene Therapy 7, 1947-54, Oct. 20, 1996.
Bandyopadhyay, Paramita, et al., "Enhanced Gene Transfer into HuH-7 Cells and Primary Rat Hepatocytes Using Targeted Liposomes and Polyethylenimine," Bio Techniques 25: 282-292, Aug. 1998.
Bettinger, Thierry, et al, "Size Reduction of Galactosylated PEI/DNA Complexes Improves Lectin-Mediated Gene Transfer into Hepatocytes," Bioconjugate Chemistry, 1999, 10, 558-561.
Bieber, Thorsten, et al., "Preparation of Low Molecular Weight Polyethylenimine for Efficient Cell Transfection," BioTechniques 30: 74-81 Jan. 2001).
Blessing, Thomas, "Different Strategies for Formation of PEGylated EGF-Conjugated PEI/DNA Complexes for Targeted Gene Delivery," Bioconjugate Chemistry 2001, 12, 529-37.
Boussif, Otmane, et al, "A Versatile Vector for Gene and Oligonucleotide Transfer Into Cells In Culture and In Vivo: Polyethylenimine," Proc. Nat'l. Acad. Sci. USA, vol. 92, 7297-7301, Aug. 1995.
Bronich, Tatiana K., et al., Self-assembly in Mixtures of Poly(ehtylene oxide)-graft- Poly(enthyleneimine) and Alkyl Sulfates, Langmuir, 1998, 14, 6104-106.
Coll, Jean-Luc, et al., "In Vivo Delivery to Tumors of DNA Complexed with Linear Polyethylenimine," Human Gene Therapy, 10, 1659-66, Jul. 1, 1999.

(Continued)

Primary Examiner—Richard Schnizer
(74) Attorney, Agent, or Firm—Kenyon & Kenyon LLP

(57) ABSTRACT

The present provides a carrier molecule for transporting a polyanioic macromolecule such as a nucleic acid across a biological barrier of a cell. The carrier has a biocompatible backbone polymer with two or more polycationic polymer fragments covalently linked. In one embodiment, the backbone polymer is polyethylene glycol (PEG) and the polycationic polymer is polyethylenimine (PEI). The copolymer carrier molecule can be complexed with a polyanionic macromolecule such as a nucleic acid (NA). The NA/copolymer complex is stable in biological conditions by forming a special coreshell-like micelle structure. The nucleic acid can be rapidly released from the complex when biodegradation linker are used to bind the polycationic polymer fragments to the polymer backbone. The carriers and complexes of the invention can be used tin methods of delivering the polycainonic macromolecules to cells both in vitro and in vivo.

50 Claims, 1 Drawing Sheet

OTHER PUBLICATIONS

De Smedt, Steffan C., et al., "Cationic Polymer Based Gene Delivery System," Pharmaceutical Research, vol. 17, No. 2, 2000, 113-126.

Dheur, Sonia et al., "Polyethylenimine but Not Cationic Lipid Improves Antisense Activity of 3'-Capped Phosphodiester Oligonucleotides," Antisense & Nucleic Acid Drug Development, 9:515-525 (1999).

Diebold, Sandra S., et al., "Mannose Polyethylenimine Conjugates for targeted DNA Delivery into Dendritic Cell" The Journal of Biological Chemistry, vol. 247, No. 27, Jul. 2, 1999, 19087-94.

Fischer, Dagmar, et al, "A Novel Non-Viral Vector for DNA Delivery Based on Low Molecular Weight, Branched Polyethylenimine: Effect of Molecular Weight on Transfection Efficiency and Cytotoxicity," Pharmaceutical Research, vol. 16, No. 8, 1999.

Godbey, W. T., et al., "Poly(ethylenimine)-mediated transfection. A new paradigm for Gene Delivery," 321-28. BioMed Mater Res., Jun. 2000.

Godbey, W. T. et al., "Size matters: Molecular Weight Affects the Efficiency of poly(ethylenimine as a Gene Delivery Vehicle," BioMed Mater Res., Jun. 1999, 5:45(3), 268-75.

Godbey, W. T., et al., "Recent Progress In Gene Delivery, Using Non-Viral Tranfer Complexes," Journal of Controlled Release 72, 2001, 115-25.

Godbey, W. T. et al., "Poly(ethylenimine) and its Role in Gene Delivery," Journal of Controlled Release, 60, (1999) 149-160.

Goula, D., et al., "Rapid Crossing of The Pulmonary Endothelial Barrier By Polyethylenimine/DNA Complexes," Gene Therapy 2000, 7, 499-504.

Han, Sand-oh, et al., "Water-Soluble Lipopolymer for Gene Delivery," Bioconjugate Chemistry, 2001, 12, 337-345.

Kirchesis, Ralf, et al,, "Design and Gene Delivery Activity of Modified Polyethylenimines," Advanced Drug Delivery Reviews, vol, 53, Issue 3, Dec. 31, 2001, 341-358.

Kircheis, Ralf, et al., "Tumor Targeting with Surface-Shielded Ligan-Polycation DNA Complexes," Journal of Controlled Release, 72, 2001, 165-170.

Liu, Feng, et al., "Glucose-Induced Release of Glycosylpoly(ethylene-glycol) Insulin Bound to a Soluble Conjugate of Concanavalin A," Bioconjugae Chem. 1997, 8, 664-72.

Ngyuen, H-K, et al., "Evaluation of Polyether-polyethyleneimine Graft Copolymers as Gene Transfer Agents," Gene Therapy 2000, 7, 126-138.

Park, Y.K., et al., "Galatosylated Chitosan-Graft-Dextran as Hepatocyle-Targeting DNA Carrier," Journal of Controlled Release, 69, 2000, 97-108.

Pouton, Colin W., et al., "Key Issues in Non-Viral Gene Delivery," Advanced Drug Delivery Reviews 46 (2001) 187-203.

Robaczewka, M., et al., "Inhibition of Hepadnaviral Replication By Polythylenimine-based Intravenous Delivery of Antisense Phosphodiester Oligodeoxynucleotides to Liver," Gene Therapy, 2001, 8, 874-881.

Vinogradov, Serguei V., et al., "Self-Assembly of Polyamine-Poly(ethylene glycol) Copolymers with Phosphorothioate Oligonucleotides," Bioconjugate Chem. 1996, 9, 805-812.

Wagner, Ernst, "Application of Membrance-Active Peptides for Nonviral Gene DeLivery," Advanced Drug Delivery Reviews, 38, (1999) 279-289.

Yu, Lei, et al., "TerplexDNA Gene Carrier System Targeting Artery Wall Cells," Journal of Controlled Release, 72, (2001), 179-189.

Ming Kung et al, Surface Modifications of Alginate/Poly(L-Lysine) Microcapsular Membranes with Poly(Ethylene Glycol) and Poly(Vinyl Alchohol), Biomaterials, vol. 16, No. 8, 1995.

* cited by examiner

SEQUENCE LISTING

<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 1

Gly Phe Leu Gly
1

<210> SEQ ID NO 2
<211> LENGTH: 4
<212> TYPE: PRT

-continued

```
<213> ORGANISM: Artificial Sequence
<220> FEATURE:
<223> OTHER INFORMATION: synthetic polypeptide

<400> SEQUENCE: 2

Gly Phe Phe Gly
1
```

POLYCATIONIC WATER SOLUBLE COPOLYMER AND METHOD FOR TRANSFERRING POLYANIONIC MACROMOLECULES ACROSS BIOLOGICAL BARRIERS

BACKGROUND OF THE INVENTION

1. The Field of the Invention

The present invention relates to the transport of biologically active agents across biological barriers. More specifically, the present invention relates to methods and compositions that enhance transport of polyanionic macromolecules such as DNA, RNA, antisense oligonucleotides and their analogs across biological barriers.

2. Technical Background

Gene therapy and antisense technology have been highly promoted for their potential to treat or cure a number of diseases. Many viral diseases and genetic conditions can potentially be treated by gene therapy. A great number of genes that play a role in previously untreatable diseases such as cancer, autoimmune diseases, cystic fibrosis and the like have been discovered. With the discovery of the gene involved, researchers have determined that the disease can be treated by either blocking a gene that is being overexpressed or by providing a copy of a malfunctioning gene. Often these treatments require the administration of DNA, RNA, antisense oligonucleotides, and their analogs to achieve a desired intracellular effect.

These treatment strategies have been shown to block the expression of a gene or to produce a needed protein in cell culture. However, a major problem with these promising treatments, is adapting them for use in vivo. For a compound to be an effective pharmaceutical agent in vivo, the compound must be readily deliverable to the patient, not rapidly cleared from the body, have a tolerable level of toxicity, and be able to reach the site within the body where it is needed.

However, macromolecules such as DNA, RNA, antisense oligonucleotides, and their analogs share similar, significant pharmaceutical problems. While these compounds are generally not toxic, if there are admistered orally, they do not reach the desired site because they are digested and metabolized. Injection of these polyanionic macromolecules increases the length of time the molecules are in the body, but does not target the specific area of need. Moreover they are subject to rapid degradation within the blood stream and clearance from the body.

Because DNA, RNA, and oligonucleotides are polyanionic macromolecules they do not readily cross biological barriers. The transfer of these materials into living cells is the major impediment to their use as therapeutic agents. An effective gene and oligonucleotide delivery system will need to bind to an appropriate cell, be internalized by endocytosis, escape from the lysosome and ultimately transfer the intact free DNA or oligonucleotides to the nucleus or plasma. In another words, the success of gene therapy and antisense therapy is largely dependent on achieving a delivery of nucleic acids in sufficient quantities, to the correct target site of action, and for the desired time frame.

Many different strategies, including both viral and non-viral systems, have been attempted for the effective delivery of genes and oligonucleotides. Each of these strategies has had varying degrees of success. However, none of them are safe and efficient enough for clinical use. Toxicity, transfection efficiency, nucleic acid (NA) degradation and free NA release are challenging problems for all of the current non-viral gene delivery systems, including liposomes and cationic polymers.

A particular problem with non-viral delivery systems is the balance between the stability of the NA/carrier complex and the ability of the carrier to release the NA in the targeted cell. The NA/carrier complex must be stable enough to remain intact in the circulation system, but yet unstable enough to release the free NA at the target site.

One approach that has been used to allow entry of the polyanionic macromolecules to the cell cytoplasm is complexing the polyanionic macromolecule to a highly polycationic polymer such as PEI. PEI is a highly polycationic synthetic polymer. It has been used for years in common processes such as paper production, shampoo manufacturing, and water purification. Recently, PEI has become one of the most successful polycation carriers used in oligonucleotide and DNA delivery.

PEI has been shown to be a highly efficient carrier for delivering oligonucleotides and plasmids, both in vitro and in vivo. PEI is available in both linear and branched forms. Because of its high positive charge density, PEI spontaneously forms interpolyelectrolyte complex (Polyion complex) with nucleic acid as a result of cooperative electrostatic interaction between the ammonium groups of the PEI and the phosphate groups of the nucleic acid. The ability of PEI to transfect a wide variety of cells is well established. Compared to other polycationic carriers, PEI has proved to be much better in protecting against nucleic acid degradation and releasing the nucleic acid to the cytoplasm after endocytosis.

The transfection mechanism has been explored by different laboratories, but still is not quite clear. It is generally accepted that PEI transfection of cells begins with the entry of PEI via endocytosis. Then the complex or the PEI buffers the acidic pH of the lysosome, protecting the nucleic acid degradation and causing an osmotic swelling/rupture of the vesicles. The rupture of the vesicle releases the nucleic acid into the cytoplasm. The dissociation of free nucleic acid from the cationic polymer is generally assumed to be accelerated by the replacement of cellular polyanionic molecules. It is believed that protonation of the PEI leads to an expansion of the polymeric network due to the intramolecular charge repulsion.

However, PEI is not a perfect transfecting agent. For example, the PEI/NA complex usually produces serious aggregations in physiological buffers. Moreover, the complexes show limited stability in the presence of serum and are rapidly cleared out of the bloodstream following systemic administration. Moreover, PEI has been consistently observed to be toxic both in vitro and in vivo. These properties have significantly limited the biomedical applications of PEIs.

To partially overcome the toxic effects of the PEI and the aggregation problems of the PEI/NA complex in biological buffers, the polymer has been conjugated or grafted with both hydrophilic and hydrophobic groups. Grafting of the PEIs with PEG results in copolymers that can form relatively stable DNA complexes in aqueous buffers. However, transfection activity of these systems is much lower than that of unmodified PEI (25 kDa). Partially propionyl acylated liner PEI (50 kDa and 200 kDa) also shows less toxicity, but again this modification compromises the transfection activity. Conjugation of targeting groups, such as transferrin, mannose, and galactose, increased the transfection efficiencies toward targeted tissue, but still do not solve the intrinsic toxicity problems associated with high molecular PEIs, because high molecular PEIs have to be used as precursors in order to get efficient transfection activities. Small sized PEIs are much less toxic, but unfortunately low molecular weights PEIs (less than 2,000 Dalton) were found to produce no or very low transfection activities in various conditions.

In light of the foregoing, it would be an advancement in the art to provide a method of delivering polyanionic macromolecules to target cells. It would be an additional advancement to provide a carrier molecule that could efficiently transport the polyanionic macromolecules to across biological barriers. A further advancement would be achieved if the carrier molecule showed reduced toxicity as compared to presently available compounds. It would be a further advancement if the carrier/macromolecule complex were stable exhibited serum stability. It would be a further advancement if carrier/macromolecule complex could readily disassociate within the target cell. It would be a further advancement to provide a carrier molecule that could be targeted to a specific tissue or cell type.

BRIEF SUMMARY OF THE INVENTION

This invention provides a novel class of polycation grafted biocompatible copolymers which can be used as carrier molecules to deliver a polyanionic macromolecule to a cell. Two or more polycationic polymer fragments are covalently linked to a biocompatible hydrophilic backbone polymer by linkers. The number of polycationic polymer fragments bound to the backbone polymer may be in the range from about 4 to about 100. It has been found that a number of polycationic fragments in the range from about 8 to about 15 can be successfully used to bind a polyanionic macromolecule and transfer the polyanionic macromolecule across biological barriers such as a cell wall or a plasma membrane. A variety of biocompatible polymers maybe used as the backbone polymer. The backbone polymer may be, for example, polyethylene glycol (PEG), poly (N-(2-hydroxylpropyl)methacrylamide), or copolymers thereof. Likewise a variety of polycationic polymers maybe linked to the backbone polymer. The polycationic polymer may be, for example, polyalkylamine (PAM), polyethylenimine (PE), polylysine (PL), a polypeptide, chitosan, a polysaccharide, or copolymers thereof.

The carrier molecule may also include at least one targeting moiety connected to the biocompatible hydrophilic backbone or to the polycationic polymer. The targeting moiety can be selected to bind to a specific biological substance or site. Thus, the targeting moiety can be chosen based on its ability to bind to a molecule expressed in a specific cell type or specific tissue allowing the polyanionic macromolecule to be selectively delivered to the cell or tissue. Such targeting moieties may include a ligand, an antigen, a hapten, biotin, lectin, galactose, galactosamine, a protein, a histone, a polypeptide, a lipid, a carbohydrate, a vitamin, and a combination thereof.

The carrier molecule may also include at least one lysis agent connected to the biocompatible hydrophilic backbone or to the polycationic polymer. The lysis agent can be selected to break down a biological membrane such as a cell, endosomal, or nuclear membrane, thereby allowing the polyanionic macromolecule to be released into the cytoplasm or nucleus of the cell. Such lysis agents may include a viral peptide, a bacterial toxin, a lytic peptide, aleveolysin, bifermentolysin, boutulinolysin, capriciolysin, cereolysin O, chauveolysin, histolyticolysin O, pneumolysin, sealigerolysin, septicolysin O, sordellilysin, streptoslysin O, tenaolysin or thuringolysin O, and active fragments thereof.

As mentioned previously, the polycationic polymers are covalently linked to the biocompatible backbone polymer by linkers. The targeting moiety and the lysis agent may also be covalently linked to the backbone polymer by a linker. Such linkers can be a hydrocarbon chain, a PEG fragment, a polypeptide, a linear polymer containing an ester bond, a linear polymer containing an amide bond, a linear polymer containing a disulfide bond, a linear polymer containing a hydrozone bond, a linear polymer containing an oxime bond or a combination thereof. The linkers can be biodegradable peptides that can be broken by chemicals or enzymes to release the polycationic polymer, the targeting moiety, or the lysis agent from the backbone polymer. Examples of such biodegradable peptide are GlyPheLeuGly (SEQ. ID. NO.: 1) and GlyPhePheGly (SEQ ID. NO.: 2). The linkers can have a length from about 2 to about 100 atoms. Linkers with a length of about 3 atoms to about 30 atoms can also be used.

The biocompatible hydrophilic backbone can have a molecular weight that is selected to optimize the delivery of the polyanionic macromolecule to the cell. Thus, in certain embodiments the backbone polymer has a molecular weight in the range from about 1,000 to about 1,000,000. A backbone polymer with a molecular weight in the range from about 5,000 to about 100,000 may also be used. A biocompatible hydrophilic backbone with a molecular weight of about 20,000 to about 40,000 can be used to deliver the polyanionic macromolecule to the cell.

The molecular weight of the polycationic polymers can also be selected for optimal delivery of the polyanionic macrcomolecule to the target cell. The molecular weight can be in the range from about 100 about 100,000. Alternatively the molecular weight of the polycationic polymers can be in the range from about 200 to about 10,000. A polycationic polymer with a molecular weight in the range from about 400 to about 2,000 can be used to deliver the polyanionic macromolecule to the cell.

The present invention also relates to a complex for delivering a polyanionic macromolecule to a cell. The complex may have a carrier molecule as described above complexed with a polyanionic macromolecule. The complex maybe given to an animal in vivo or a cell culture. The complex allows the polyanionic macromolecule to be delivered to a cell within the animal or cell culture.

The polyanionic macromolecule can be selected from a number of macromolecules that are useful in the treatment of disease or in laboratory experimentation. In certain configurations of the complex, the polyanionic macromolecule is a nucleic acid such as RNA, DNA, or a combination or derivative thereof. The nucleic acid can be, for example, genomic DNA, plasmid DNA, synthetic DNA, or RNA. Other types of nucleic acids that can be used with the carrier molecule of present invention are, for example, an antisense oligonucleotide, ribozyme, DNAzyme, chimeric RNA/DNA oligonucleotide, phosphorothioate oligonucleotide, 2'-O-methyl oligonucleotides, DNA-PNA conjugates, DNA-morpholino-DNA conjugates, and combinations thereof.

The invention also provides a method of transporting a polyanionic macromolecule across a biological barrier of a cell. The biological barrier can be a cell wall, a plasma membrane, or like cell membrane. The cell maybe for example a cell in a cell culture. Alternatively the cell maybe a cell within a multicellular organism such as a plant or an animal. The cell can be a cell derived from an organism such as hepatocytes, liver cells, kidney cells, brain cells, bone marrow cells, nerve cells, heart cells, spleen cells, stem cells and co-cultures of the above. Moreover, the cells may be from established cell lines such a HepG Hep G2 and Hela cells. The method of transporting the polyanionic macromolecule across the barrier includes complexing the polyanionic macromolecule to a carrier molecule of the present invention to create a complex. The cell is then contacted with the carrier molecule to deliver the polyanionic macromolecule to the cell. The complex is then taken into the cell by, for example, endocytocis and then released into the cell cytoplasm.

BRIEF DESCRIPTION OF THE DRAWINGS

A more particular description of the invention briefly described above will be rendered by reference to specific embodiments thereof which are illustrated in the appended drawings. These drawings depict only typical embodiments of the invention and are not therefore to be considered to be limiting of its scope. The invention will be described and explained with additional specificity and detail through the use of the accompanying drawings in which.

DETAILED DESCRIPTION OF THE PREFERRED EMBODIMENTS

Figure 1:
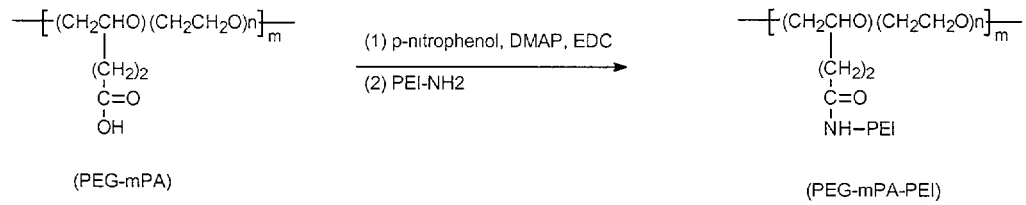
FIG. 1A is a schematic representation of the synthesis of one embodiment of a polycation grafted biocompatible copolymer of the present invention.
FIG. 1B is a schematic representation of the synthesis of another embodiment of a polycation grafted biocompatible copolymer of the present invention.
Figure 1:
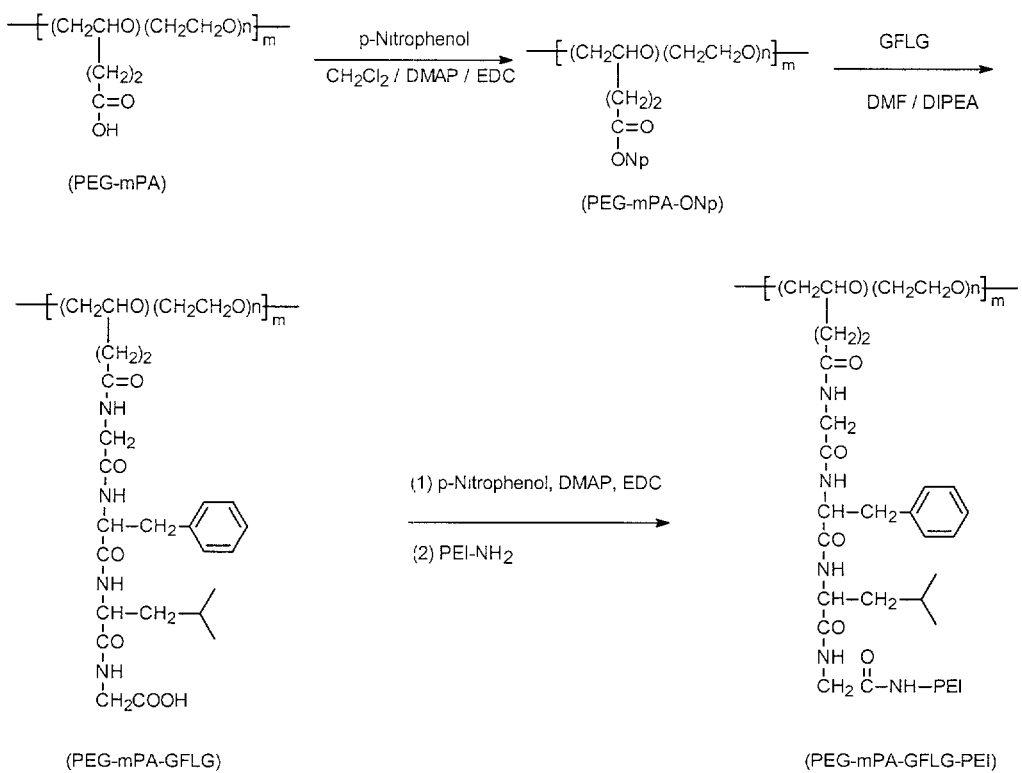
Figure 1:
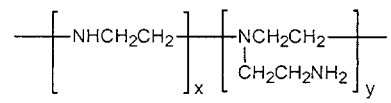

This invention provides a novel class of polycation grafted biocompatible copolymers which can be used as carrier molecules to deliver a polyanionic macromolecule to a cell. Two or more polycationic polymer fragments are randomly covalently linked to a biocompatible hydrophilic backbone polymer by a linker. The number of polycationic polymer fragments bound to the backbone polymer may be in the range from about 4 to about 100. It has been found that a number of polycationic fragments in the range from about 8 to about 15 can be successfully used to bind a polyanionic macromolecule and transfer the polyanionic macromolecule across biological barriers. As used herein biocompatible refers to a substance that has limited immunogenic and allergenic ability. Biocompatible also means that the substances does not cause significant undesired physiological reactions. A biocompatible substance may be biodegradable. As used herein biodegradable means that a substance such as the backbone polymer or the polycationic polymer can chemically or enzymatically break down or degrade within the body. A biodegradable substance may form nontoxic components when it is broken down. Moreover, the biocompatible substance can be biologically neutral, meaning that it lacks specific binding properties or biorecognition properties.

A variety of biocompatible polymers may be used as the backbone polymer. The backbone polymer may be, for example, polyethylene glycol (PEG), poly (N-(2-hydroxylpropyl)methacrylamide), or copolymers thereof. Likewise a variety of polycationic polymers maybe linked to the backbone polymer. The polycationic polymer maybe, for example, polyalkylamine (PAM), polyethylenimine (PEI), polylysine (PL), a polypeptide, chitosan, a polysaccharide, or copolymers thereof.

PEG has many qualities that make it a desirable biocompatible backbone polymer for use with the carrier polymers of the invention. First, PEG is commercially available in a variety of molecular masses at low dispersity (Mw/Mn<1.1). Based on their molecular size, PEG polymers are arbitrarily classified into low molecular weight PEG (Mw<20,000) and high molecular weight PEG (Mw>20,000). A recent study found that the renal clearance of PEG decreased with an increase in molecular weight, with the most dramatic change occurring at a MW of 30,000 after intravenous administration. The halftime($t\frac{1}{2}$) of PEG circulating in blood also showed a concomitant and dramatic increase. For instance, the $t\frac{1}{2}$ for PEG went from approximately 18 min to 16.5 hour as the molecular weight increased from 6,000 to 50,000. Consequently, conjugation of anticancer drugs with PEG of a molecular weight of 20,000 or greater can prevent rapid elimination of the PEG-conjugated species and allow for passive tumor accumulation The carrier molecule may also include at least one targeting moiety connected to the biocompatible hydrophilic backbone or to a bound polycationic polymer. The targeting moiety can be selected to bind to a specific biological substance or site herein referred to as the receptor. Thus, the targeting moiety can be chosen based on its ability to bind to a receptor molecule expressed in a specific cell type or specific tissue allowing the polyanionic macromolecule to be selectively delivered to the cell or tissue. The targeting moiety can be any signal member which is recognizable by a cell membrane receptor. Thus, in certain embodiments, the targeting moiety is a galtactose containing saccharide which specifically binds to liver cells or hepatoma cells. The galactose containing sacchride can be selected from the group consisting of lactose and galactose A targeting moiety refers to those moieties that bind to a specific biological substance or site. The biological substance or site is considered the target of the targeting moiety that binds to it. Ligands are one type of targeting moiety. Ligands have a selective (or specific) affinity for another substance known as the receptor. Because the ligand has a specific affinity for the receptor, the ligand binds to the receptor selectively over other molecules. Thus, when a ligand is used in conjunction with the carrier polymer of the present invention, the carrier polymer can be designed to bind to a receptor on a specific cell type. This selective binding allows for the selective delivery of the polyanionic macromolecule to the target cell. Examples of ligands suitable for targeting cells are antigens, haptens, biotin, biotin derivatives, lectins, galactose, galactosamine vitamin and fucosylamine moieties, receptors, substrates, coenzymes and cofactors among others.

When applied to the polycation grafted copolymers of this invention, a ligand includes an antigen or hapten that is capable of being bound by, or to, its corresponding antibody or an active fraction thereof. Also included are viral antigens or hemagglutinins and neuraminidases and nucleocapsids including those from any DNA viruses, RNA viruses, HIV, hepatitis viruses, adenoviruses, alphaviruses, arenaviruses, coronaviruses, flaviviruses, herpesviruses, myxoviruses, oncornaviruses, papovaviruses, paramyxoviruses, parvoviruses, picornaviruses, poxviruses, reoviruses, rhabdoviruses, rhinoviruses, togaviruses, and viriods. The ligand maybe selected from any bacterial antigens including those of gram-negative and gram-positive bacteria, acinetobacter, achromobacter, bacteroides, clostridium, chlamydia, enterobacteria, haemophilus, lactobacillus, neisseria, staphyloccus, and streptoccocus. Other suitable ligands include any fungal antigens such as those of aspergillus, candida, coccidiodes, mycoses, phycomycetes, and yeasts. Other antigens such as mycoplasma antigens, rickettsial antigens, protozoan antigens, and parasite antigens are suitable ligands in certain embodiments of the invention. Human antigens including those of blood cells, virus infected cells, genetic markers, oncoproteins, plasma proteins, complement factors, alphafetoprotein, prostate specific antigen (PSA), cancer markers, and rheumatoid factors may also serve as suitable ligands.

There are many other substances that may be used as appropirate ligands to direct the carrier copolymer to the target cell. Among these substances are proteins, histones, hormones, vitamins, steroids, prostaglandins, synthetic or natural polypeptides, carbohydrates, lipids, antibiotics, drugs, digoxins, pesticides, narcotics, and neurotransmitters. Ligands also refers to various substances with selective affinity for a that are produced through recombinant DNA, genetic and molecular engineering.

The receptor for a ligand is an important consideration in selecting a ligand to target a cell. The receptor may also be referred to as a ligator, binding body, or a binding partner. The receptor functions as a type of biorecognition molecule that selectivley binds to the ligand. The receptor is molecule that is generally, but not necessarily, larger than the ligand that binds it. A receptor can be a protein such as an antibody or a non-protein binding body. As used herein an antibody refers to all classes of antibodies including monoclonal antibodies, chimeric antibodies, Fab fractions, and derivatives thereof. Other receptors suitable for targeting include naturally occurring receptors, hemagglutinins, and cell membrane and nuclear derivatives that bind specifically to hormones, vitamins, drugs, antibiotics, cancer markers, genetic markers, viruses, and histocompatibility markers. Another group of receptors includes RNA and DNA binding proteins. Other potentially useful receptors for targeting are cell surface enzymes such as neuraminidases, plasma proteins, avidins, streptavidins, chalones, cavitands, thyroglobulin, intrinsic factor, globulins, chelators, surfactants, organometallic substances, staphylococcal protein A, protein G, ribosomes, bacteriophages, cytochromes, lectins, certain resins, and organic polymers. Receptors also include various substances such as any proteins with selective affinity for ligands that are produced through recombinant DNA and genetic and molecular engineering.

The carrier molecule may also include at least one lysis agent connected to the biocompatible hydrophilic backbone or to a bound polycationic polymer. The lysis agent could be any membrane fusion peptide or protein. The lysis agent can be selected to break down a biological membrane such as a cell, endosomal, or nuclear membrane, thereby allowing the polyanionic macromolecule to be released into the cytoplasm or nucleus of the cell. As a result of the presence of the lysis agent, the membrane undergoes lysis, fusion, or both. Such lysis agents may include a viral peptide, a bacterial toxin, a lytic peptide, alveolysin, bifermentolysin, botulinolysin, cereolysin O, chauveolysin, histolyticolysin O, pneumolysin, seeligerolysin, septicolysin O, sordellilysin, streptolysin O, tenolysin or thuringolysin O, and active fragments thereof. A lytic peptide is a chemical grouping which penetrates a membrane such that the structural organization and integrity of the membrane is lost. Lysis agents also include viruses and synthetic compounds that can break down a biological membrane. Fragments of the above listed lysis agents which will provide endosomal escape activity may also be employed in the present invention. Other peptides and proteins are known to cause the breakdown or fusion of biological membranes and maybe used as a lysis agent within the scope of the invention. Jahn, R. & Sudhof T., *Annu. Rev. Biochem.* 68: 863–911 (1999). Pecheur, E. I., et al, *J Membrane Biol.* 167: 1–17 (1999).

As mentioned previously, the polycationic polymer is covalently linked to the biocompatible backbone polymer by a linker. The targeting moiety and the lysis agent may also be covalently linked to the backbone polymer or the bound polycationic polymer by a linker. Such linkers can be a hydrocarbon chain, a PEG fragment, a polypeptide, a linear polymer containing an ester bond, a linear polymer containing an amide bond, a linear polymer containing a disulfide bond, a linear polymer containing a hydrozone bond, a linear polymer containing an oxime bond or a combination thereof. The linkers may either be biodegradable linkers or non-biodegradable linkers. Examples of biodegradable linkers are short peptides and disulfide linkers ($-(CH_2)xSS(CH_2)x-$ wherein x is an integer of 2 to 8). Non-biodegradable linkers include hydrocarbon linkers such as $-(CH_2)n-$ or $-(CH_2CH_2O)n-$ where n is an integer of 2 to 50. The linkers can have a length from about 2 to about 100 atoms. Linkers with a length of about 3 atoms to about 30 atoms can also be used.

The linkers used to covalently link the polycationic polymer to the backbone polymer can be configured to allow for the controlled release complexed polyanionic macromolecule from the carrier. Controlled release indicates that the nucleic acid or other polyanionic macromolecule is released from the copolymer carrier complex only by cleavage of the linker that were used to synthesize the carrier. Thus, controlled release does not include the release of the polyanionic macromolecule by diffusion until the linkages are cleaved.

Biodegradable linkers include, but are not limited to, two categories of bonds. A first category includes disulfide linkages and ester bonds. Disulfide linkages and ester bonds are known for covalent coupling of pharmaceutical compounds to polymers. However, this category of bonds has limited value for delivering pharmaceutical compounds in vivo because these bonds are subject to cleavage in the blood stream. The second category includes bonds that are generally cleaved after entering the cell (intracellular cleavage). This category of linkers are cleavable under acidic conditions like those found in lysosomes or by enzymes thereby allowing the pharmaceutical compound to be released intracellularly.

The bonds that are cleaved under acidic conditions are known as acid-sensitive or acid-liable bonds. One example of an acidsensitive bond is a hydrazone linkage. Greenfield, et al, *Cancer Res.* 50: 6600–6607 (1990). Enzyme-sensitive linkers include polypeptides that contain amino acid sequences that make the polypeptide hydrophobic. These polypeptides are cleaved by specific enzymes such as cathepsins, found primarily inside the cell. Such polypeptides can be synthetic or naturally occurring peptides. Examples of suitable biodegradable polypeptide linkers are GlyPheLeuGly (SEQ. ID. NO.: 1) and GlyPhePheGly (SEQ. ID. NO.: 2). Another type of biodegradable linkage is a "hindered" or "protected" disulfide bond that sterically inhibits attack from thiolate ions. Such protected disulfide bonds are found in the coupling agents S-4-succinimidyloxycarbonyl-.alpha-.methyl benzyl thiosulfate (SMBT) and 4-succinimidyloxycarbonyl-.alpha-.methyl-.alpha.-(2-pyridyldithio) toluene (SMPT).

The biocompatible hydrophilic backbone can have a molecular weight that is selected to optimize the delivery of the polyanionic macromolecule to the cell. Thus, in certain embodiments the backbone polymer has a molecular weight in the range from about 1,000 to about 1,000,000. A backbone polymer with a molecular weight in the range from about 5,000 to about 100,000 may also be used. A biocompatible hydrophilic backbone with a molecular weight of about 20,000 to about 40,000 can be used to deliver the polyanionic macromolecule to the cell.

The molecular weight of the polycationic polymer can also be selected for optimal delivery of the polyanionic macromolecule to the target cell. The molecular weight can be in the range from about 100 about 100,000, Alternatively the molecular weight of the polycationic polymer can be in the range from about 200 to about 10,000. A polycationic polymer with a molecular weight in the range from about 400 to about 2,000 can be used to deliver the polyanionic macromolecule to the cell.

The present invention also relates to a complex for delivering a polyanionic macromolecule to a cell. Once the complex is delivered to the cell, the carrier molecule allows the complex to cross the cell wall and other biological barriers and gain access to the interior of the cell. The complex may have a carrier molecule as described above complexed with a polyanionic macromolecule. The complex may be given to an animal in vivo or to a cell in culture. The complex allows the polyanionic macromolecule to be delivered to the a cell within the animal or cell culture.

The polyanionic macromolecule can be selected from a number of macromolecules that are useful in the treatment of disease or in laboratory experimentation. In certain configurations of the complex, the polyanionic macromolecule is a nucleic acid such as RNA, DNA, or a combination or derivative thereof. The nucleic acid can be, for example, genomic DNA, plasmid DNA, synthetic DNA, or RNA. Other types of nucleic acids that can be used with the carrier molecule of present invention are, for example, an antisense oligonucleotide, ribozyme, DNAzyme, chimeric RNA/DNA oligonucleotide, phosphorothioate oligonucleotide, 2'-O-methyl oligonucleotides, DNA-PNA conjugates, DNA-morpholino-DNA conjugates, and combinations thereof.

The invention also provides a method of transporting a polyanionic macromolecule across the biological barriers of the cell. The cell maybe for example a cell in a cell culture. Alternatively the cell maybe a cell within a multicellular organism such as a plant or an animal. The cell can be a cell derived from an organism such as hepatocytes, liver cells, kidney cells, brain cells, bone marrow cells, nerve cells, heart cells, spleen cells, stem cells and co-cultures of the above. Moreover, the cells may be from established cell lines such a HepG Hep G2 and Hela cells.

The method of delivering the polyanionic macromolecule to the cell includes complexing the polyanionic macromolecule to a carrier molecule of the present invention to create a complex. The cell is then contacted with the complexed carrier molecule to deliver the polyanionic macromolecule to the cell. The carrier complex may enter the cell by endocytocis and then escape from the vesicles to gain access to the cytoplasm of the cell. If the target cell is within a cell culture in vitro, the cell can be contacted with the complexed carrier molecule by providing the cells with a growth medium containing the polyanionic macromolecule/carrier complex or by inserting a solution containing the polyanionic macromolecule/carrier complex into the growth media. If the target cell is within an organism in vivo, the contacting may occur by positioning the complex within the organism so that it has access to the target cell. For example, the complex maybe administered by injecting a solution containing the complex into the circulatory system of the organism. A carrier molecule with a targeting moiety attached will allow the complex to be directed to a target cell with a target corresponding to the targeting moiety. The polyainonic macromolecule/carrier complex may be administered to an organism by intramuscular, intraperitoneal, intraabdominal, subcutaneous, intravenous, and intraarterial delivery. Other methods of administration of the complex include parenteral, topical, transdermal, transmucosal, inhaled, and insertion into a body cavity such as by ocular, vaginal, buccal, transurethral, rectal, nasal, oral, pulmonary, and aural administration.

When the polymeric carrier molecules of the invention are complex with a nucleic acid or other drugs, they form polymeric micelles. Following intravenous administration, such polymeric micelles have been found to have a prolonged systemic circulation time. This prolonged circulation time is due to their small size and hydrophilic shell which minimize uptake by the mononuclear phagocyte system and to their high molecular weight which prevents renal excretion. Polymeric micelle incorporated drugs may accumulate in tumors to a greater extent than the free drug and show reduced distribution into untargeted areas such as the heart. Accumulation of polymeric micelles in malignant or inflamed tissues may be due to increased vascular permeability and impaired lymphatic drainage. The tumor vessels are more leaky and less permselective than normal vessels. Several in vivo studies have shown that polymeric micelles are able to improve the efficiency of anticancer drugs against leukemia and solid tumors. The studies indicated that PEG does not exhibit specific affinity for any organ and that its accumulation in tumor tissue is mainly governed by the level of hyperpermeable tumor vasculature (enhanced permeability retention or EPR effect), irrespective of the molecular mass of the polymer and the tumor loading site.

The EPR effect is considered as a passive targeting method, but drug targeting could be further increased by binding to targeting moieties such as antibodies or sugars or by introducing a polymer sensitive to variation in temperature or pH. Targeting micelles or pH sensitive micelles can serve for the delivery of drug to tumors, inflamed tissues or endosomal compartments, since they all are associated with a lower pH than normal tissue.

A solution of the grafted copolymer that contains nucleic acid or other polyanionic macromolecules can administered to the cultured cells or the body. An important consideration in the usefulness of a carrier molecules is how much drug can be loaded into the carrier. The molar ratio of the nitrogen on the carrier copolymer to the phosphate on the nucleic acid (the N/P ratio) should be considered. In most instances the N/P ratio in the complexes of the carrier polymer and nucleic acid molecules will be in the range of about 1 to about 50. More specifically, it is anticipated that for most uses the N/P ratio in the complexes will be in the range between about 2 to about 30. These ranges given above are not exclusive of the N/P ratio that may be used with the invention. As long as functionality is maintained, drug loadings outside of these ranges falls within the scope of the invention.

Referring to FIG. 1A, the general synthesis of a carrier copolymer of the present invention is illustrated. Polyethylene glycol (PEG) of mean molecular weight is obtained. The PEG has a number "m" of pendant propionic acid groups (PA) randomly grafted onto its backbone. PEG-mPA and anhydrous dichloromethane are combined with the protection of argon. Then p-nitrophenol and 4-dimethylaminopyridine (DMAP) are added to the solution. Then 1-[3-dimethylaminopropyl]-3-ethylcarbodiimide hydrochloride (EDC) is added to form a clear solution. Then acetic acid is added to the clear mixture. The clear reaction mixture is then mixed with a Solution of polyethylenimine (PE) in anhydrous dimethylformamide (DMF) under the protection Of argon. The mixture maybe concentrated on a rotary evaporator to remove most of the DMF solvent. The resulting product can be purified and concentrated to produce a wax product. The crude wax product can be further purified on a gel filtration column to yield purified PEG-mPA-PEI.

Referring to FIG. 1B, the general synthesis of another carrier polymer of the present invention is illustrated. This carrier polymer is formed from a PEG backbone conjugated to PEI via a biodegradable polypeptide linker, GFLG. PEG-mPA is obtained as a starting material. The PEG-mPA is then converted to PEG-mPA-ONp. PEG-mPA-ONp is synthesized by dissolving PEG-mPA in anhydrous dichloromethane. Then p-nitrophenol and 4-dimethylaminopyridine (DMAP) are added. Then 1-[dimethylaminopropyl]-3-ethylcarbodiimide hydrochloride (EDC) is added. Next acetic acid is added to the solution. Then p-Toluenesulfonic acid monohydrate is added to neutralize the DMAP catalyst. The reaction yields a white product that is PEG-mPA-ONp.

The PEG-mPA-ONp product and GFLG tetrapeptide are then dissolved in anhydrous DMF. N,N-diisopropylethylamine (DIPEA) is added to this solution. The reaction mixture can be concentrated to remove excess solvent. Cold ethyl ether may be added to precipitate the product. The PEG-mPA-GFLG product is then purified. The PEG-mPA-GFLG product is reacted with polyethylenimine to form PEG-mPA-GLFG-PEI.

EXAMPLES

The following examples are given to illustrate various embodiments which have been made within the scope of the present invention. The following examples are neither comprehensive nor exhaustive of the many types of embodiments which can be prepared in accordance with the present invention.

Materials and General Methods

PEG with pendant propionic acid groups (PEG-8PA PEG-10PA, and PEG-15PA, Mw=~20 KD, SunBio, Inc., Anyang City, South Korea) was dried overnight in vacuo at room temperature. PEI600 (Mw=600), PEI1200 (Mw=1,200), PEI2K (Mw=1,800) and PEI10K (Mw=10,000) were from Polysciences, Inc. of Warrington, Pa. PEI400 (Mn=423), PEI800 (Mw=800) and PEI25K (Mw=25,000) were purchased from Aldrich Chemical Company, Inc. of Milwaukee, Wis. Other chemicals were from Aldrich or VVR and used as received without further purification. HPLC analysis was performed on a Waters system equipped with Waters RI detector and Phenomenex Polysep-GPC-P 3000 column. $^1$H-NMR was recorded on a Varian 400 MHz machine.

Example 1

Synthesis of PEG20K-15PA-PEI400 (15 PEI400 grafted PEG-20K)

A dry 50 ml one necked flask was charged with 1.3 g of polyethylene glycol of mean molecular weight of about 20,000 with 15 pendant propionic acid groups (PEG20K-15PA) (~0.75 mmole pendant —COOH, dried overnight in vacuum in $P_2O_5$ desiccator) and 10 ml anhydrous dichloromethane with the protection of argon. About 0.15 g (1.1 mmoles) of p-nitrophenol and about 0.015 g of 4-dimethylaminopyridine were added to the flask. The mixture was stirred at room temperature to form a clear solution. Then about 0.20 g (1.0 mmoles) of fine powdered 1-[3-dimethylaminopropyl]-3-ethylcarbodiimide hydrochloride (EDC) was added in one portion. The mixture was again stirred for about 2 hours at room temperature following the dissolution of EDC. Then about 0.18 ml (3.2 mmoles) of acetic acid was added to the clear mixture. The mixture was stirred for an additional 30 minutes at room temperature. The clear reaction mixture was mixed with a solution of 20 ml of linear PEI 400 (Aldrich 46,853-3, Mn=~423) in 20 ml anhydrous dimethylformamide (DMF) with vigorous stirring under protection of argon. The mixture was stirred at room temperature for about 4 hours, then concentrated on a rotary evaporator to remove most of the DMF solvent. The oil mixture was then diluted with water and purified on a gel filtration column (Sephacryl S-100,2.5×90 cm). The desired copolymer fractions were pooled together after HPLC analysis. About 1.5 g of pure product was obtained. $^1$H-NMR analysis indicated that the copolymer contains about 10% (w/w) PEI, indicating that the average molecular weight of the copolymer was about 23,444 assuming the average molecular weight of the starting PEG15PA is 20,000. $^1$H-NMR ($D_2O$, 400 MHz), •3.4–3.8 (m, 100 (arbitrarily set), —$CH_2CH_2O$— of PEG), 2.4–3.2 (m, 12, —$CH_2CH_2N$— of PEI).

Example 2

Synthesis of PEG20K-15PA-PEI800 (15 PEI 800 grafted PEG20K)

Following the procedure of Example 1, 1.0 g of polyethylene glycol of mean molecular weight of about 20,000 with about 15 pendant propionic acid groups (PEG20K-15PA) reacted with polyethylenimine of mean molecular weight of about 800 (PEI800, 20 grams) to produce about 1.1 grams of PEI20K-15PA-PEI800. $^1$H-NMR analysis indicates that the copolymer contains about 30% (w/w) PEI, indicating that the average molecular weight of the copolymer is about 28,400, assuming the average molecular weight of the starting PEG15PA is 20,000. $^1$H-NMR ($D_2O$, 400 MHz), •3.4–3.8 (m, 100 (arbitrarily set), —$CH_2CH_2O$— of PEG), 2.4–3.2 (m, 43.0, —$CH_2CH_2N$— of PEI).

Example 3

Synthesis of PEG20K-8PA-PEI800 (8 PEI 800 grafted PEG-20K)

Following the procedure of Example 1, 1.0 gram of polyethylene glycol of mean molecular weight of about 20,000 with about 8 pendant propionic acid groups (PEG20K-8PA) reacted with polyethylenimine of mean molecular weight of about 800 (PEI800,20 grams) to produce about 1.2 grams of PEI20K-8PA-PEI800. $^1$H-NMR analysis indicates that the copolymer contains about 11.5% (w/w) PEI, which indicating that the average molecular weight of the copolymer is about 22,607, assuming the average molecular weight of the starting PEG-8PA is 20,000. $^1$H-NMR ($D_2O$, 400 MHz), •3.4–3.8 (m, 100 (arbitrarily set), —$CH_2CH_2O$— of PEG), 2.4–3.2 (m, 13.3, —$CH_2CH_2N$— of PEI).

Example 4

Synthesis of PEG-10PA-PEI1200 (10 PEI1200 grafted PEG20K)

A dry 1000 ml one neck flask was charged with 5.0 grams of PEG-10PA (mean molecular weight of about 20,000 with 10 pendant propionic acid groups, dried in $P_2O_5$ desiccator overnight), 0.56 grams of p-nitrophenol and 50 ml of anhydrous pyridine with the protection of argon. To the clear mixture was added 0.77 grams of 1-[dimethylaminopropyl]-3-ethyl carbodiimide (EDC). The mixture was stirred at room temperature for about 5 hours. Acetic acid (0.6 ml) was added with another 30 minute stirring at room temperature. The mixture was reacted with 100 ml of PEI1200 (Mw=1,200) in 200 ml of anhydrous pyridine overnight at room temperature. The mixture was concentrated to remove the pyridine solvent on a rotary evaporator. The viscous solution was diluted to about 1000 ml with deion water. The solution was ultrafiltrated to about 60 ml followed by diafiltration with 2000 ml of deion water on a Pall Filtron Minim Diafiltration system equipped with a Memrane Centramate with al OK NMWC membrane cassette (Pall Corporation, East Hills, N.Y.). The final product solution was concentrated on a rotary evaporator, about 4.5 grams of wax solid was obtained. The wax product was further purified by ether precipitation from methanol twice, about 4.1 grams of white powered PEG-10PA-PEI1200 was obtained. $^1$H-NMR analysis indicates that the copolymer contains about 20% (w/w) PEI, indicating that the average molecular weight of the co-polymer is about 24,963, assuming the average molecular weight of the starting PEG-10PA is 20,000 Dalton. $^1$H-NMR (D$_2$O, 400 MHz), •3.4–3.8 (m, 100 (arbitrarily set), —CH$_2$CH$_2$O— of PEG), 2.4–3.2 (m, 29, —CH$_2$CH$_2$N— of PEI).

Example 5

Synthesis of PEG20K-8PA-PEI2K (8 PEI1800 grafted PEG-20K)

Following the procedure of Example 1, 1.0 gram of polyethylene glycol of mean molecular weight of about 20,000 with about 8 pendant propionic acid groups (PEG20K-8PA) was reacted with polyethylenimine of mean molecular weight of about 1,800 (PEI2K, about 20 grams) to produce about 1.1 grams of PEG20K-8PA-PEI2K. $^1$H-NMR analysis indicates that the copolymer contains about 27% (w/w) PEI, indicating that the average molecular weight of the copolymer is about 27,490, assuming the average molecular weight of the starting PEG-8PA is 20,000. $^1$H-NMR (D$_2$O, 400 MHz), •3.4–3.8 (m, 100 (arbitrarily set), —CH$_2$CH$_2$O— of PEG), 2.4–3.2 (m, 38.3, —CH$_2$CH$_2$N— of PEI).

Example 6

Synthesis of PEG 20K-15PA-GFLG-PEI400 (15 PEI400 grafted PEG20K with GFLG linkers)

Referring now to FIG. 1B, PEG20K-15PA-GLFG-PEI400 was synthesized according to the illustrated scheme. PEG20K-15PA-ONp was synthesized by dissolving polyethylene glycol (PEG) of mean molecular weight of about 20,000 with about 15 pendant propionic acid groups (PEG20K-15PA) (2.0 g, ~1.5 mmole —COOH,) in 20 ml anhydrous dichloromethane. Then about 292 mg (2.1 mmoles, Fw=139) p-nitrophenol and about 26 mg (0.2 mmole) 4-dimethylaminopyridine (DMAP) were added to the solution. The mixture was stirred at room temperature to form a clear solution. Then about 402 mg (2.1 mmoles) of fine powdered 1-[dimethylaminopropyl]-3-ethylcarbodiimide hydrochloride (EDC) were added. The mixture was stirred at room temperature for about 3 hours. Next, about 0.4 ml of acetic acid was added, and the mixture was stirred for an additional 30 minutes. About 400 mg (2.1 mmoles, Fw=190.22) p-Toluenesulfonic acid monohydrate was added to neutralize the DMAP catalyst. The mixture was stirred at room temperature until all solids were dissolved. About 40 ml isopropanol was added to the solution. Then approximately 20 ml of solvent was removed in vacuum on a rotary evaporator. The flask was raised from the water bath and the products solidified as the rotating flask cooled under the influence of the vacuum. Then the suspension was cooled for 1 hour on an ice bath. A white solid was collected by vacuum filtration with the protection of argon. The filter cake was washed with a total of 20 ml ice cold 10% methanol/isopropanol followed by 10 ml of room temperature ethyl ether. The damp product is dissolved in 20 ml methanol, then slowly added to 40 ml of ice cold isopropanol on a ice bath. The white solid was filtered, washed with 10 ml of ice cold 10% methanol/isopropanol and 10 ml of room temperature of ethyl ether. The product was briefly dried with a stream of argon followed by drying in vacuum P$_2$O$_5$ desiccator overnight. About 2.0 gram of the white PEG-15PA-ONp product was obtained, and the product contains about 9.9 ONp groups per PEG-20K molecule as determined by UV absorbance (•401.5 nm=18,400 in 0.1 N NaOH solution).

About 2.0 grams (1.0 mmole ONp ester) of dried PEG20K-15PA-ONp and 608 mg (1.2 equivalents of ONp ester) of dried GFLG tetrapeptide (TFA salt) were dissolved in 20 ml of anhydrous DMF. About 0.48 ml (2.76 mmoles, 2 equivalents of GFLG) of N,N-diisopropylethylamine (DIPEA) were added to the solution. The reaction mixture was stirred at room temperature for 4 hours. The reaction mixture was concentrated to about 10 ml. To residue was added about 100 ml of cold ethyl ether to precipitate the product. The white solid was filtered off to give about 4 grams of crude product. It was purified on a gel filtration column (2.0×80 cm of Sephadex G25, eluted with 0.1 mM triethylamine/acetic acid buffer (pH=10)) to give 1.75 gram of pure product. $^1$H-NMR indicate that each copolymer molecule of a PEG20K contains about 9 GFLG tetrapeptide: $^1$H-NMR (D$_2$O, 400 MHz), •7.2 (d, 2.62, ArH of Phe), 3.4–3.8 (m, 100 (arbitrarily set), —CH$_2$CH$_2$O— of PEG), 0.78 (d, 38.3, CH$_3$ of Leu).

The purified PEG30K—15PA-GFLG product was reacted with PEI400 to form PEG20K-15PA-GFLG-PEI400. About 1.0 gram of PEG20K-1 SPA-GFLG was reacted with about 20 grams of polyethylenimine of mean molecular weight of about 400 (PEI400) as describe in Example 1. About 1.1 grams of PEG20K-15PA-GFLG-PEI2K was obtained. $^1$H-NMR indicates that each copolymer molecule contains 2,000 PEI and 9.0 molecules of GFLG linker assuming the average molecular weight of the starting PEG15PA is 20,000. $^1$H-NMR (D$_2$O, 400 MHz), δ 7.2 (m, 2.5, ArH of Phe), 3.4–3.8 (m, 100 (arbitrarily set), —CH$_2$CH$_2$O— of PEG), 2.4-3.2 (m, 10, —CH$_2$CH$_2$N— of PEI), 0.78 (d, 2.6, CH$_3$ of Leu).

Example 7

Synthesis of PEG20K-15PA-GFLG-PEI800 (15 PEI800 grafted PEG20K with GFLG linkers)

Following the procedure of Example 5, PEG20K-15PA reacted with GFLG and polyethylenimine 800 (PEI800) to produce PEG20K-15PA-GFLG-PEI800. $^1$H-NMR indicates that each copolymer molecule contains 4,400 PEI and 9.0 molecules of GFLG linker assuming the average molecular weight of the starting PEG 15PA is 20,000. $^1$H-NMR (D$_2$O, 400 MHz), δ 7.2 (m, 2.5, ArH of Phe), 3.4–3.8 (m, 100

(arbitrarily set), —CH$_2$CH$_2$O— of PEG), 2.4–3.2 (m, 22, —CH$_2$CH$_2$N— of PEI), 0.78 (d, 2.6, CH$_3$ of Leu).

Example 8

Synthesis of PEG20K-8PA-GFLG-PEI400 (8 PEI400 grafted PEG20K with GFLG linkers)

Following the procedure of Example 5, PEG20K-8PA reacted with GFLG and polyethylenimine 400 (PEG400) to produce PEG20K-8PA-GFLG-PEI400. $^1$H-NMR indicates that each copolymer molecule contains 1,087 PEI and 3.8 molecules of GFLG linker, assuming the average molecular weight of the starting PEG-8PA is 20,000. $^1$H-NMR (D$_2$O, 400 MHz), δ 7.2 (m, 1.1, ArH of Phe), 3.4–3.8 (m, 100 (arbitrarily set), —CH$_2$CH$_2$O— of PEG), 2.4–3.2 (m, 5.6, —CH$_2$CH$_2$N— of PEI), 0.78 (d, 1.1, CH$_3$ of Leu).

Example 9

Synthesis of PEG20K-8PA-GFLG-PEI800 (8 PEI800 grafted PEG20K with GFLG linkers)

Following the procedure of Example 5, PEG20K-8PA reacted with GFLG and polyethylenimine 800 (PEI800) to produce PEG20K-8PA-GFLG-PEI800. $^1$H-NMR indicates that each copolymer molecule contains 2,207 PEI and 3.8 molecules of GFLG linker assuming the average molecular weight of the starting PEG15PA is 20,000. $^1$H-NMR (D$_2$O, 400 MHz), 87.2 (m, 1.1, ArH of Phe), 3.4–3.8 (m, 100 (arbitrarily set), —CH$_2$CH$_2$O— of PEG), 2.4–3.2 (m, 11.3, —CH$_2$CH$_2$N— of PEI), 0.78 (d, 1.1, CH$_3$ of Leu).

Example 10

Synthesis of PEG20K-8PA-GFLG-PEI2K (8 PEI2K grafted PEG 20K with GFLG linkers)

Following the procedure of Example 5, PEG20K-8PA reacted with GFLG and polyethylenimine with mean molecular weight of 1800 (PEI2K) to produce PEG20K-8PA-GFLG-PEI2K. $^1$H-NMR indicates that each copolymer molecule contains 6,297 PEI and 3.8 molecules of GFLG linker, assuming the average molecular weight of the starting PEG-8PA is 20,000. $^1$H-NMR (D$_2$O, 400 MHz), δ 7.2 (m, 1.1, ArH of Phe), 3.4–3.8 (m, 100 (arbitrarily set), —CH$_2$CH$_2$O— of PEG), 2.4–3.2 (m, 26, —CH$_2$CH$_2$N— of PEI), 0.78 (d, 1.1, CH$_3$ of Leu).

Example 11

Transfection of plasmid DNA to cultured cells using copololymers

HT1080 cells were seeded on a 6-well tissue culture plate. The cells were seeded at about 100,000 cells per well in 1.0 ml of HyQ MEM/EBSS medium with 10% FBS. The plate was incubated overnight at 37° C. in a 5% CO$_2$ incubator. Next, the medium was removed by aspiration and 900 μL of fresh medium was added to each well.

A transfection medium was prepared containing a complex of DNA and a carrier copolymer of the present invention. A solution of the carrier copolymer was created. The concentration of the carrier copolymer was normalized to about 0.6 mg/ml PEI in PBS buffer. Next a volume of the carrier copolymer solution ranging from about 2.0 μL to about 20 μL was added to about 100 μL of serum free media in a sterile tube. The resulting solution was incubated for about 10 minutes at room temperature. The solution was then mixed with about 2.0 μL of 1.0 μg/μL of green fluorescent protein DNA (GFP) or red flourescent protein DNA (RFP) solution and incubated 20 minute at room temperature to create a DNA/carrier copolymer complex.

The DNA/carrier copolymer complex was added drop wise to the cells in the 6 well plate. As the complex was added to the cells, the plate was gently rocked in all directions to mix the complex with the growth medium. The cells were then incubated for at least 24 hours at 37° C. in a 5% CO$_2$ incubator. The cells were examined with a fluorescence microscope, or a FACS cell sorter. The transfection medium was removed by aspiration and fresh medium was added to preserve the cells. Table 1 shows the results of the transfection experiments using various carriers of the present invention and controls and plasmid GFP DNA. A plus indicates successful transfection and a minus indicates no transfection.

Example 12

Transfection of Oligonucleotide to Cultured Cells Using Copolymers

About 2,500 cells per well were seeded on a 96 well tissue culture plate. The cells were incubated overnight at 37° C. in a 5% CO$_2$ incubator. Then the old medium was removed by aspiration and 50 μL of fresh medium with 10% FBS was added.

A transfection medium was prepared containing the a complex of an oligonucleotide and the carrier copolymer of the present invention. A solution of the carrier copolymer was created. The concentration of the carrier copolymer was about 0.6 mg/ml PEI in PBS buffer. Next, a volume ranging from about 2.0 μL to about 20 μL of the carrier copolymer solution was added to a volume of serum free media to make a total solution volume of 50 μL in a sterile tube. The resulting solution was incubated at room temperature for about 10 minutes.

The solution was then mixed with about 2.0 μL of 0.1 mM oligonucleotide solution (22-mer, ~0.7 mg/ml). The oligonucleotide contained was a 22-mer phosphodiester oligonucloetide with a 3' inversion and 5' fluorescence labeling. The resulting transfection medium was then incubated for 20 minutes at room temperature. The transfection medium was added to the wells in the 96 well plate. The cells were then incubated at 37° C. in a 5% CO$_2$ incubator for about 6 hours. Next, the transfection medium was removed by aspiration and the cells were washed twice with about 100 μL of sterile PBS.

After washing, about 100 μL of fresh medium was added to the wells and the cells were viewed under fluorescence micro scope. Fluorescence indicated that the cells were successfully transfected with the oligonucleotide. Table 1 shows the results of the transfection experiments using different carriers of the present invention and controls and the oligonucleotide. A plus indicates successful transfection and a minus indicates no transfection. Table 1. Summary of the copolymer structures and their transfection activities on plasmid DNA and oligonucleotides. The chemical structures were carefully characterized using $^1$H-NMR on a Varian 400 MHz machine. The DNA and oligonucleotide binding stability was tested by gel shift assay as described. Gene transfection was tested using plasmid DNA containing GFP reporting gene. Oligonucleotide transfection was tested using a 22-mer phosphodiester oligonucleotide with 3'-end inversion and 5'-end fluorescence labeling.

| Copolymer | $N_{(GFLG)}$ | $W_{(PEI)}$ | Mw | DNA/oligo Binding | Transfection psDNA | Transfection Oligo |
|---|---|---|---|---|---|---|
| PBG-15PA-PEI400 | 0.0 | 2,344 (10%) | 23,444 | + | − | − |
| PEG-15PA-PEI800 | 0.0 | 8,400 (30%) | 28,400 | + | + | + |
| PEG-8PA-PEI800 | 0.0 | 2,607 (11.5%) | 22,607 | + | − | + |
| PEG-10PA-PEI1200 | 0.0 | 4,963 (20.0%) | 24,936 | + | + | + |
| PEG-8PA-PEI2K | 0.0 | 7,490 (27%) | 27,490 | + | + | + |
| PEG-15PA-GFLG-PEI400 | 9.0 | 2,000 (7.8%) | 25,400 | − | − | − |
| PEG-15PA-GFLG-PEI800 | 9.0 | 4,400 (15.8%) | 27,900 | + | + | + |
| PEG-8PA-GFLG-PEI400 | 3.8 | 1,087 (4.8%) | 22,577 | + | − | + |
| PEG-8PA-GFLG-PEI800 | 3.8 | 2,207 (9.3%) | 23,697 | + | + | + |
| PEG-8PA-GFLG-PEI2K | 3.8 | 4,975 (18.8%) | 26,465 | + | + | + |
| Controls: | | | | | | |
| PBI-25K (from Sigma) | | | 25,000 | + | + | + |
| PEI-2K (from Polysciences) | | | 1,800 | + | − | + |
| PEI-400 (from Sigma) | | | 400 | − | − | − |

SUMMARY

In summary, the invention presents a novel class of polycation grafted polymeric carrier molecules. The novel polycation grafted copolymers exhibit substantial water solubility and a low level of toxicity. Certain embodiments of the invention uses PEG as a backbone polymer to which PEI fragments or other polycationic polymer fragments are attached. PEG is linear polymer with many useful properties, such as good solubility and good excretion kinetics. Additionally, PEG is biocompatibility because of its minimal toxicity, immunogenicity and antigenicity. These features have made PEG the most extensively studied drug carrier in pharmaceutical research which had been approved by FDA for internal administration. By conjugating a polycationic polymer to a biocompatible polymers such as PEG, the polycationic polymer can be rendered more soluble and less toxic. Additionally small polycationic polymer fragments are much less toxic than large molecular weight cationic polymers and could be easily cleared out from the body. Thus, by conjugating the small cationic polymers to a biocompatible backbone polymer carrier copolymers can be created that allow for delivery of therapeutics such as polyanionic macromolecules to cells.

The carrier polymers of the present invention also provide enhanced stability of the complexed DNA/carrier copolymer stability. The carrier polymers of the present invention have also been to shown to have enhanced transfection activity compared to other DNA carrier polymers. Unlike the unmodified polycations which form aggregation precipitates when complexed with nucleic acids, the copolymers of this invention bind nucleic acids through ionic interaction to form a coreshell like micelle structure. This structure is stable and soluble in biological conditions due to the neutral hydrophilic shell formed by the biocompatible backbone polymer. The complex is stable in biological buffers, even with the presence of serum. As a result, the transfection activity is much higher than the unmodified polycation carriers, such as PEI, PLL or chitosan.

The carriers of the present invention can be used to deliver drugs and other therapeutic agents to specifically targeted cells or tissues. The copolymer carrier can be used for the controlled release and targeted delivery of nucleic acids to a cell. Moreover, the efficiency of a drug efficiency can be increased by targeting specific cells or organs, therefore reducing accumulation of the drug in healthy tissues and minimizing its toxicity. Such specific targeting allows higher doses of a therapeutic to be administered, if needed, without undesired effects on non targeted cells

---

I claim:

1. A carrier molecule for transporting a polyanionic macromolecule across a membrane of a cell consisting of:
   a single polyethylene glycol (PEG) backbone polymer; and
   about 4 to about 100 polyethylenimine (PEI) polymers covalently linked to the PEG backbone polymer by linkers.

2. The carrier of claim 1, further comprising at least one targeting moiety connected to the PEG backbone polymer or to one of the about 4 to about 100 PEI polymers.

3. The carrier of claim 2, wherein the at least one targeting moiety is selected from the group consisting of a ligand, an antigen, a hapten, biotin, a lectin, galactose, galactosamine, a protein, a histone, a polypeptide, a lipid, a carbohydrate, a vitamin, and a combination thereof.

4. The carrier of claim 1, further comprising at least one lysis agent connected to the PEG backbone polymer or to one of the about 4 to about 100 PEI polymers.

5. The carrier of claim 4, wherein the at least one lysis agent is selected from the group consisting of a viral peptide, a bacterial toxin, a lytic peptide, alveolysin, bifermentolysin, botulinolysin, cereolysin O, chauveolysin, histolyticolysin O, pneumolysin, seeligerolysin, septicolysin O, sordelliysin, streptolysin O, tenolysin or thuringolysin O, and active fragments thereof.

6. The carrier of claim 1, wherein the linkers are about 2 to about 100 atoms in length.

7. The carrier of claim 6, wherein the linkers are selected from the group consisting of a hydrocarbon chain, a PEG fragment, a polypeptide, a linear polymer containing an ester bond, a linear polymer containing an amide bond, a linear polymer containing a disulfide bond, a linear polymer containing a hydrozone bond, and a linear polymer containing an oxime bond.

8. The carrier of claim 6, wherein the linkers are about 3 atoms to about 30 atoms in length.

9. The carrier of claim 1, wherein the PEG backbone polymer has a molecular weight in the range from about 1,000 to about 1,000,000 daltons and the about 4 to about 100 PEI polymers have a molecular weight in the range from about 100 to about 100,000 daltons.

10. The carrier of claim 9, wherein the molecular weight of the PEG backbone polymer is in the range from about 5,000 to about 100,000 daltons.

11. The carrier of claim 9, wherein the molecular weight of the PEG backbone polymer is in the range from about 20,000 to about 40,000 daltons.

12. The carrier of claim 9, wherein the molecular weight of the about 4 to about 100 PEI polymers is in the range from about 200 to about 10,000 daltons.

13. The carrier of claim 9, wherein the molecular weight of the about 4 to about 100 PEI polymers is in the range from about 400 to about 2,000 daltons.

14. The carrier of claim 1, wherein from about 8 to about 15 PEI polymers are covalently linked to the PEG backbone polymer by linkers.

15. The carrier of claim 1, wherein the molecular weight of the PEG backbone polymer is in the range from about 20,000 to about 40,000 daltons.

16. The carrier of claim 1, wherein the molecular weight of the about 4 to about 100 PEI polymers is in the range from about 400 to about 2,000 daltons.

17. The carrier of claim 1, wherein the linkers are selected from the group consisting of a hydrocarbon chain, a PEG fragment, a polypeptide, a linear polymer containing an ester bond, a linear polymer containing an amide bond, a linear polymer containing a disulfide bond, a linear polymer containing a hydrozone bond, and a linear polymer containing an oxime bond.

18. The carrier of claim 1, comprising a linker which is a biodegradable peptide.

19. The carrier of claim 18, wherein the biodegradable peptide is selected from the group consisting of GlyPhePheGly (SEQ ID NO.2) and GlyPheLeuGly (SEQ ID NO.1).

20. A complex for transporting a polyanionic macromolecule across a membrane of a cell comprising:
   a carrier molecule for delivering the polyanionic macromolecule to the cell, the carrier molecule consisting of a single poly (N-(2-hydroxypropyl)methacrylamide) (HPMA) backbone polymer and two or more PEI polymers covalently linked to the poly (N-(2-hydroxypropyl)methacrylamide) (HPMA) backbone polymer by linkers; and
   a nucleic acid complexed with the carrier molecule.

21. The complex of claim 20, wherein the nucleic acid is selected from the group consisting of genomic DNA, plasmid DNA, synthetic DNA, and RNA.

22. The complex of claim 20, wherein the nucleic acid is selected from the group consisting of an antisense oligonucleotide, a ribozyme, a DNAzyme, a chimeric RNA/DNA, a phosphorothioate oligonucleotide, a 2'-O-methyl oligonucleotide, a DNA-PNA conjugate, a DNA-morpholino-DNA conjugate, and a combination thereof.

23. The complex of claim 20, wherein the HPMA backbone polymer has a molecular weight in the range from about 1,000 daltons to about 1,000,000 daltons and the PEI polymers have a molecular weight in the range from about 100 daltons to about 100,000 daltons.

24. The complex of claim 23, wherein the molecular weight of the HPMA backbone polymer is in the range from about 20,000 daltons to about 40,000 daltons.

25. The complex of claim 24, wherein the molecular weight of the PEI polymers is in the range from about 400 daltons to about 2,000 daltons.

26. The complex of claim 20, wherein the linkers are selected from the group consisting of a hydrocarbon chain, a PEG fragment, a polypeptide, a linear polymer containing an ester bond, a linear polymer containing an amide bond, a linear polymer containing a disulfide bond, a linear polymer containing a hydrozone bond, and a linear polymer containing an oxime bond.

27. The complex of claim 20, further comprising at least one targeting moiety connected to the HPMA backbone polymer or to one of the two or more PEI polymers, the at least one targeting moiety selected from the group consisting of a ligand, an antigen, a hapten, biotin, a lectin, galactose, galactosamine, a protein, a histone, a polypeptide, a lipid, a carbohydrate, and a combination thereof.

28. The complex of claim 20, further comprising at least one lysis agent connected to the HPMA backbone polymer or to one of the two or more PEI polymers, the at least one lysis agent selected from the group consisting of a viral peptide, a bacterial toxin, a lytic peptide, alveolysin, bifermentolysin, botulinolysin, cereolysin O, chauveolysin, histolyticolysin O, pneumolysin, seeligerolysin, septicolysin O, sordellilysin, streptolysin O, tenolysin or thuringolysin O, and active fragments thereof.

29. The complex of claim 20, wherein from about 4 to about 100 PEI polymers are covalently linked to the HPMA backbone polymer by linkers.

30. The complex of claim 20, wherein from about 8 to about 15 PEI polymers are covalently linked to the HPMA backbone polymer by linkers.

31. A method of transporting a polyanionic macromolecule across a membrane of a cell comprising:
(a) complexing the polyanionic macromolecule to a carrier molecule to create a
complex, the carrier molecule consisting of a single biocompatible hydrophilic backbone polymer and two or more polycationic polymers covalently linked to the biocompatible hydrophilic backbone polymer by a biodegradable peptide linkers which are from about 2 to about 100 atoms in length, wherein the biocompatible hydrophilic backbone polymer is selected from the group consisting of PEG and HPMA; and
(b) contacting the cell with the complex.

32. The method of claim 31, wherein the polycationic polymers are selected from the group consisting of polyalkylamine (PAM), polyethylenimine (PEI), a polylysine (PL), a polypeptide, chitosan, a polysaccharide, and copolymers thereof.

33. The method of claim 31, further comprising at least one targeting moiety connected to the biocompatible hydrophilic backbone or to one of the two or more polycationic polymers, the at least one targeting moiety selected from the group consisting of a ligand, an antigen, a hapten, biotin, a lectin, galactose, galactosamine, a protein, a histone, a polypeptide, a lipid, a carbohydrate, and a combination thereof.

34. The method of claim 31, further comprising at least one lysis agent connected to the biocompatible hydrophilic backbone polymer or to one of the two or more polycationic polymers, the at least one lysis agent selected from the group consisting of a viral peptide, a bacterial toxin, a lytic peptide, aleveolysin, alveolysin, bifermentolysin, botulinolysin, capriciolysin, cereolysin O, chauveolysin, histolyticolysin O, pneumolysin, seeligerolysin septicolysin O, sordellilysin, streptolysin O, tenolysin or thuringolysin O, and active fragments thereof.

35. The method of claim 31, wherein the biodegradable peptide linker is selected from the group consisting of GlyPhePheGly (SEQ ID NO.2) and GlyPheLeuGly (SEQ ID NO.1).

36. The method of claim 31, wherein the biocompatible hydrophilic backbone has a molecular weight in the range from about 1,000 to about 1,000,000 daltons and the polycationic polymers have a molecular weight in the range from about 100 to about 100,000 daltons.

37. The method of claim 36, wherein the molecular weight of the biocompatible hydrophilic backbone is in the range from about 20,000 to about 40,000 daltons.

38. The method of claim 36, wherein the molecular weight of the polycationic polymers is in the range from about 400 to about 2,000 daltons.

39. The method of claim 36, wherein the biocompatible hydrophilic backbone is polyethylene glycol and the polycationic polymers are polyethylenimine.

40. The method of claim 39, wherein the molecular weight of the biocompatible hydrophilic backbone is in the range from about 20,000 to about 40,000 daltons.

41. The method of claim 39, wherein the molecular weight of the polycationic polymers is in the range from about 400 to about 2,000 daltons.

42. The method of claim 31, wherein from about 4 to about 100 polycationic polymers are covalently linked to the biocompatible hydrophilic backbone polymer by the biodegradable peptide linkers.

43. The method of claim 31, wherein from about 8 to about 15 polycationic polymers are covalently linked to the biocompatible hydrophilic backbone polymer by the biodegradable peptide linkers.

44. A carrier for transporting a polyanionic macromolecule across a membrane of a cell comprising:
a PEG biocompatible hydrophilic backbone polymer; and
two or more PEI polycationic polymers covalently linked to the PEG biocompatible hydrophilic backbone polymer by peptide or propionic acid linkers;
wherein the PEI polycationic polymers have a molecular weight of from about 400 to about 2,000 daltons.

45. The carrier of claim 44 wherein the PEI polycationic polymers have a molecular weight of about 2,000 daltons.

46. The carrier of claim 44 wherein the PEI polycationic polymers have a molecular weight of about 1,200 daltons.

47. The carrier of claim 44 wherein the PEI polycationic polymers have a molecular weight of about 800 daltons.

48. The carrier of claim 44 wherein the PEI polycationic polymers have a molecular weight of about 400 daltons.

49. The carrier of claim 44, wherein the linkers are a peptide and the peptide is selected from the group consisting of GlyPhePheGly (SEQ ID NO. 2) and GlyPheLeuGly (SEQ ID NO. 1).

50. The carrier of claim 44, wherein the molecular weight of the PEG biocompatible hydrophilic backbone polymer is in the range from about 20,000 to about 40,000 daltons.

* * * * *